US005601921A

United States Patent [19]
Eriksson

[11] Patent Number: 5,601,921
[45] Date of Patent: Feb. 11, 1997

[54] ALUMINIUM-SALT IMPREGNATED FIBRES, A METHOD FOR THEIR MANUFACTURE, FLUFF CONSISTING OF SUCH FIBRES, AND THE USE OF THE FIBRES AS ABSORPTION MATERIAL

[75] Inventor: Inger V. Eriksson, Sundsvall, Sweden

[73] Assignee: Molnlycke AB, Goteborg, Sweden

[21] Appl. No.: 266,618

[22] Filed: Jun. 28, 1994

Related U.S. Application Data

[63] Continuation of Ser. No. 842,147, filed as PCT/SE90/00623 Sep. 27, 1990 published as WO91/05106 Apr. 18, 1991, abandoned.

[30] Foreign Application Priority Data

Sep. 27, 1989 [SE] Sweden ................................. 8903180
Jul. 20, 1990 [SE] Sweden ................................. 9002475

[51] Int. Cl.$^6$ ........................................................ B32B 9/00
[52] U.S. Cl. ................... 428/389; 162/181.2; 162/181.3; 162/181.6
[58] Field of Search ........................... 428/240, 283, 428/288, 289, 389; 604/365, 367, 374, 375; 162/181.1, 181.3, 181.2, 181.6

[56] References Cited

U.S. PATENT DOCUMENTS 3,935,363 1/1976 Burkholder et al. ................... 428/281
4,584,357 4/1986 Harding ................................ 525/54.21
5,127,994 7/1992 Johansson ............................ 162/168.3

FOREIGN PATENT DOCUMENTS 0276200 7/1988 European Pat. Off. .
1424692 2/1976 United Kingdom .
WO88/06659 9/1988 WIPO .

OTHER PUBLICATIONS

"U.S. Market Outlook for Consumer Absorbent Products", Nonwovens World, Sep. 1988, By J. Carroll, pp. 51–53.
"Designing better Superabsorbent Baby Diapers", Nonwovens World, May–Jun. 1987, By J. Hanson, pp. 69–74.
"Breathable Absorbent Disposables—Market Developments and the Future", Nonwovens World, Nov. 1986, By J. Hanson, pp. 102–108.

Primary Examiner—Christopher Raimund
Attorney, Agent, or Firm—Young & Thompson

[57] ABSTRACT

Aluminum salt impregnated organic pulp fibers for use in absorption articles are disclosed. The fibers have an aluminum content of 3–100 g/kg based on the weight of dry pulp. The pulp fibers are in the form of fluff and, when disposed in a layer, exhibit increased absorption rates and improved dispersion of liquid in horizontal and vertical directions. The fibers, in the form of an aqueous suspension, are impregnated with aluminum salt in aqueous solution at a pH of 5–11, preferably 8.5–9.5 and most preferably at a pH of 9. Impregnation may optionally be carried out in the presence of a silicate.

22 Claims, No Drawings

ALUMINIUM-SALT IMPREGNATED FIBRES, A METHOD FOR THEIR MANUFACTURE, FLUFF CONSISTING OF SUCH FIBRES, AND THE USE OF THE FIBRES AS ABSORPTION MATERIAL

This application is a continuation of application Ser. No. 07/842,147, filed as PCT/SE90/00623 Sep. 27, 1990 published as WO91/05106 Apr. 18, 1991, now abandoned.

FIELD OF THE INVENTION

The present invention relates to the field of absorption materials, and in particular to the field of sanitary articles, such as diapers, incontinence guards, drying cloths (wipes) and the like, said absorbent material containing fibres that have been been impregnated with an aluminium salt and which have a high absorption rate. The invention also relates to a method of manufacturing such fibres, the use of such fibres in the form of fluff or in mixture with untreated fibres in the form of fluff, for the purpose of obtaining improved absorption.

BACKGROUND OF THE INVENTION

It is known that the fibres of cellulosic material, for instance paper pulp, lose their strength potential in the process of being dried, possibly resulting in so-called swelling collapse of the fibres. This can also be observed as an impaired ability to swell in water, and can be explained, for example, by the fact that strong hydrogen bonds are newly formed between hydrophilic groups in the fibre walls. This influences the absorption properties of the fibres, so as to reduce their absorption rate, absorption capacity and water retention properties.

It is also known to impregnate cellulosic fibres with a combined aluminium salt and silicon compound. This is described in BE 461 156 (U.S. Pat. No. 5,127,994), according to which an aluminium compound is introduced into stock which contains at least 50% fibres at pH 4–10, whereafter there is added a known mixture of polymeric silica, obtained by acidifying waterglass, and a polymeric cationic retention agent. It is stated that the polymeric silica used must present a high specific surface area, namely a specific area which exceeds 1050 $m^2$/g. The purpose of adding this combination of chemicals is to improve retention and dewatering when manufacturing paper by forming and dewatering a suspension of cellulosic fibres and filler on a forming wire.

The Swedish published specification SE-446 995 (corresponding to Swedish Patent Application No. 7900587-2) teaches a method of precipitating hydratised aluminium-silicate compounds onto fibres. This process is intended to modify the surfaces of inorganic fibres which are mixed with cellulose fibres or other organic fibres, with the intention of improving the bond between the organic and inorganic fibres so that the mechanical strength properties of the composite product will not be impaired. By treating the mixture of suspended inorganic and organic fibres first with aluminium sulphate and then with 0.05–10% by weight alkali silicate at a pH-value of 3–8, silicate is precipitated onto the inorganic fibres, thereby improving their ability to bond to the organic fibres, the resultant material being used to manufacture paper or board having good fire-retarding and dimension-stable properties.

A generally known problem within the field of the manufacture of absorbent materials for use primarily in the production of sanitary articles, such as diapers, incontinence guards etc., is one of achieving optimum absorption rates and liquid dispersion properties the fibre material of the fluff.

SUMMARY OF THE INVENTION

This problem is solved in accordance with the present invention with a material that comprises fibres which have been impregnated with aluminium-salt.

The invention thus also relates to a method of producing the fibres, the use of the fibres in fluff intended for absorption purposes, and a sanitary articles containing such fibres.

It has thus been found that fibres can be treated solely with an aluminium-salt solution without a silicate addition, at a certain pH-value and therewith provide a material which results in a higher absorption rate, even though the presence of silicate will further improve this property. The fibres also exhibit high aluminium contents of about 0.20–100 g/kg, especially 0.3–40 g/kg, particularly 0.5–20 g/kg and preferably 1.0–15 g/kg, calculated on dry fibre pulp, these contents in the case of non-treated fibres normally only being about 0.02–0.15 g/kg.

The aluminium salt used is a water-soluble aluminium salt, preference being given to poly(aluminium chloride), poly(aluminium sulphate), sodium aluminate and other basic aluminium compounds, and mixtures thereof.

pH is adjusted by adding an alkaline substance, for instance NaOH, or in some cases an acid, for instance hydrochloric acid, to obtain a pH-value of 5–11, preferably 8.5–9.5, optimally a pH of 9.

According to one preferred embodiment, poly(aluminium chloride) and the strongly alkaline sodium aluminate are added to the system in such proportions as to obtain the aforesaid pH-values without adding NaOH.

When the addition of solely sodium aluminate results in a pH-value which exceeds the desired values, it may be necessary to lower the pH, or it may also be possible to obtain a pH-value which is satisfactory from the beginning, without needing to adjust the pH with separate additions to the system, depending on the original pH-value of the pulp suspension.

pH adjustment or control is an important parameter of the present invention, since the absorption properties of the fibres become very poor when the pH lies on the acid side, i.e. a pH lower than 5. The precipitates are more compact at low pH-values, which impairs the liquid transport properties of the fibres in a dry state.

It has also been found that the aforesaid treatment of the fibres with aluminium salt is favoured by the presence of silicate. The silicate can be added in the form of an alkali silicate, e.g. waterglass, or may already be present in the fibres in the form of residues of the silicate used to stabilise hydrogen peroxide in a bleaching process. If silicate is added, the order in which the silicate and the aluminium salt are added to the system is unimportant.

However, a silicate addition is not necessary to achieve a significant increase in absorption rate, but affords a further improvement of this value. The treatment process can achieve a marked increase in absorption rate, from about 2 ml/s in the case, for instance, of untreated CTMP-pulp, and about 3.4 ml/s in the case of chemically untreated pulp, to values of about 4–5.5 ml/s. For instance, it has been found that the absorption rate of the inventive fibres impregnated with aluminium-salt solution is improved by a factor of 1.3–4, preferably 1.5–3 and the absorption rate is improved by a factor of 2 in the case of cellulosic fibres intended for conventional cellulose fluff.

The quantity of aluminium present during the impregnating process is very significant, and the higher the aluminium content the better the absorption properties obtained. Of the aluminium added to the suspension, it is possible to achieve a retention as large as from 50% up to 100% of the added amount of aluminium precipitated onto the fibres. The silicate thus has a subordinate significance and may optionally have the form of residues from the bleaching stage, which in such cases may be sufficient to produce an improved effect.

The fibres impregnated with aluminium salt may consist of many different types of fibres. They may be cellulosic fibres originating from CTMP-pulp or chemical pulp, for instance. The fibres may also consist of synthetic fibres, for instance polyester fibres, which are at present preferred, although they may also consist of polypropylene, polyamide, polyacrylonitrile, polyurethane and polyvinyl alcohol fibres. Other fibres of a vegetable origin can be used, for instance fibres from coconuts, flax, fruit, grass, moss, peat etc.

The invention also relates to a method for producing the inventive fibres impregnated with aluminium salt, in which cellulose fibres in the form of an aqueous suspension are impregnated with aluminium salt at a pH of 5–11, preferably 8.5–9.5, optimally at pH=9, optionally in the presence of silicate.

Thus, in accordance with one embodiment of the inventive method, silicate can be present when impregnating the fibres with aluminium salt.

In the case of one preferred embodiment of the invention, the process is carried out in two stages, wherein in the first stage alkali silicate is caused to diffuse into the fibre walls by impregnating the fibres with an alkali silicate solution, said fibres being in a suspension which contains at least 2% fibres, preferably at least 10%, and suitably at least 20%. The alkali silicate solution has a pH of 10.0–13 and the process of impregnation takes place while vigorously agitating the suspension. The fibre suspension is then dewatered and treated in a second stage with an aluminium salt solution at a pH of 6–11, preferably 8.5–9.5 particularly pH 9, causing the silicate to precipitate onto the fibres walls in situ, and then dewatering the suspension and drying the fibres. It is important that the pH of the suspension is above 10.0 during the alkali-silicate impregnation process, so that no silicate will precipitate before the alkali-silicate solution has had time to penetrate the cellulose fibres.

Because the fibre walls contain precipitated chemicals, there is obtained protection against swelling collapse, by which is meant a phenomenon in which the fibres lose their liquid-absorption and liquid-retention capacity when the fibres are dried, so as to become unusable as absorption material.

This chemical treatment can be effected at high fibre concentrations in kneader mixers or in conventional mixing equipment at average to low pulp concentrations or consistencies.

Impregnation with an alkali-silicate solution is preferably carried out under vacuum conditions, created by means of a vacuum pump, a diffusion pump or the like, and for the purpose of improving impregnation, i.e. penetration of the chemicals into the fibre walls, the fibre material can be passed to a retention vessel or treatment vessel prior to dewatering the suspension, where the suspension is kept for a period of time sufficient to ensure that diffusion of alkali silicate into the fibre walls is as complete as possible.

The molar ratio of OH/Al in the aluminium-salt solution is preferably 0.5–3.0.

The fibres are preferably treated immediately after the pulp has been defibered in a pulp refiner.

Subsequent to being treated with the aluminium-salt solution, the fibre suspension can be thinned with water and made alkaline to a pH-value above 8.0.

The inventive material can also be used to produce a fluff consisting of a mixture of the aluminium-salt impregnated fibres and untreated fibres normally used in products of this kind. Because of its good dispersion properties, the inventive fibre material can also replace, either completely or partially, or supplement the superabsorbents normally used in this field, therewith avoiding the risk of the blockaging effects that occur when high proportions of super-absorbents are used, as a result of their very pronounced swelling ability.

Tests have indicated that an addition of silicate is essential for increasing the absorption rate of treated fibres of this kind. It has now been found, in accordance with the invention, that it is the aluminium addition which affords the desired effect, and not the silicate addition, particularly when polyaluminium ions are added, while the possible presence of silicate has a lesser significance. The reasons for this have not been fully established, although it is theoretically conceivable that two exchange mechanisms occur between aluminium chloride and cellulose fibres, namely an ion exchange of aluminium ions with cations which are associated with the carboxyl group on the fibre, and also the formation of aluminium flocs. The sequence in which these processes take place has not been established. The mutual magnitude of these two mechanisms is contingent, among other things, on the extent to which the aluminium chloride is neutralized. The exchange between aluminium ions and hydroxyl ions results in electrically charged hydroxyl ammonium polymers. These highly charged complex aluminium compounds favour the coagulation of negative particles.

Polyaluminium ions would seem to function more effectively than normal aluminium ions. This may possibly be due to their high ion charge. The smallest quantity of metal ions required to coagulate negatively charged particles is called the critical coagulation concentration (CCC). The critical coagulation concentration decreases by a factor of 40 with the increase of the metal-ion charge in each stage of said increase. Since the concentration of polyaluminium solutions is very high, this would explain the superior properties of such solutions in comparison with normal aluminium ions. The aluminium silicate complex is negatively charged at basic pH-values and thus binds different cations as counter ions.

The invention also relates to the use of impregnated fibres as liquid-absorbent material in the form of fluff, or in mixture with fluff consisting of untreated fibres, in sanitary articles, such as diapers, incontinence guards, etc.

In accordance with one variant of the inventive method, the fluff is moistened with water which contains aluminium salt.

In the manufacture of diapers, the fluff is normally stored in a silo for instance, prior to being laid-out in the form of an absorbent layer in the diaper manufacturing machine, where the fluff is sprayed with water in order to moisten the fibres. This avoids dust formation and also facilitates compression of the fluff.

The aluminium salt used in accordance with the invention to impregnate the fibres can be mixed with the water sprayed onto the fibres, and thereafter precipitated at pH=9 or directly precipitated onto the fibres. An additional spraying stage with aluminium-salt solution can be carried out.

The invention also relates to an absorbent material which incorporates the aforedescribed inventive fibres impregnated with aluminium salt. Due to the splendid dispersion properties of the fibre material, both with respect to direction and speed, a layer of the impregnated fibres, for instance in the form of a fluff layer, or in an homogenous mixture with untreated fluff, exhibits a very high liquid absorbency, which is of particularly great significance when using such material in sanitary articles, such as diapers, incontinence guards. etc. There is obtained in this way a dry surface and improved properties with regard to repeated wetting of the material, due to the fact that the inventive fibres apparently transport liquid in the surface layer on the actual fibres themselves, which means that an absorption layer comprised of said fibres presents improved liquid dispersion in the horizontal direction of the layer, in comparison with untreated fibres.

The invention will be described still further in the following, with reference to a number of examples. The test methods and chemicals used in the tests described were as follows:

The amount of liquid absorbed over a given period of time was registered automatically, while at the same time registering the thickness of the sample body when subjected to a load of 2.5 kPa. The absorption rate is determined through the linear, initial liquid absorption phase. The sample bodies were produced in accordance with a method devised by J. W. Brill, "New Scandinavian Fluff Test Methods", TAPPI Journal, Vol. 66, No. 11, 1983.

The measuring method and apparatus used for measuring absorption rates and absorption capacity comprised "The Porous Plate Testing Apparatus" described in detail in Textile Res. J. 37 pages 356–366, 1967 by Burgeni and Kapur, "Capillary Sorption Equilibria in Fiber Masses".

All recited chemical quantities relate to contents or proportions based on pulp weight. If nothing is mentioned to the contrary, the pulp has been dried at 60° C. and defibered in a Kamas mill. When defibering the pulp, an 8 mm screen was used and the input speed was 2 g/s.

The reference pulps were subjected to the same treatment as the modified pulps, but without the chemical addition.

Used in the examples are expressions such as "aluminium-salt fibre or silicate fibre" and "precipitation", by which is meant "fibres impregnated with aluminiumsalt (or silicate") and that aluminium ions have bonded to (precipitated on) the fibres. The term "precipitation" also includes "flocculation" of an aluminium complex.

| Chemicals used | Chemical Supplier |
| --- | --- |
| Sodium metasilicate-5-hydrate | KEBO |
| Poly(aluminium sulphate) PAS 70P (aluminium 8.5%) | KEMIRA |
| Poly(aluminium chloride) PAX 11 S (aluminium 6.8%) | KEMIRA |
| Poly(aluminium chloride) PAX 11 S (aluminium 5.9%) | KEMIRA |
| Soda waterglass, ratio % by weight $SiO_2$/% by weight $Na_2O$ 1.6 | EKA |

The CTMP-pulp used was bleached with peroxide to a brightness of 70% ISO and had a freeness of 600 CSF.

EXAMPLE 1

Chemical Pulp Fibre Impregnated with Poly(Aluminium Sulphate)

Experimental Data

Pulp: Bleached softwood sulphate pulp
Pulp concentration: 3%

1. Impregnating with Waterglass

Waterglass: 20% sodium metasilicate
Impregnating time: 30 min.
Dewatering of the pulp after impregnation.

2. Impregnating with Poly(Aluminium Sulphate)

Poly(aluminium sulphate): 3–8% (aluminium conc.)
Impregnating time: 30 min.
pH of the washing water was 11 and 3 respectively.
The pulp was dried at room temperature and defibered in a Braun Multimix.

TABLE I

| Pulp sample | Results | | |
| --- | --- | --- | --- |
| | Network strength (N) | Wash water pH | Absorption rate (ml/s) |
| 0 reference | | | 1.6 |
| sample | | 3 | 3.6 |
| sample | | 11 | 4.3 |
| 2 reference | | | 3.1 |
| sample | | 11 | 4.8 |
| 4 reference | 3.7 | | 4.3 |
| sample | 4.3 | | 4.9 |

These tests show that the absorption rate increases markedly when treating chemical sulphate pulp with waterglass and poly(aluminium sulphate).

EXAMPLE 2

CTMP-Pulp Fibres were Impregnated with Poly(Aluminium Sulphate)

Experimental Data

Pulp: CTMP
Pulp consistency: 2%
The pulp was taken from dewatering press after the bleaching stage.

1. Impregnating with Waterglass

Waterglass: 10% sodium metasilicate
Impregnating time: 30 min.
The pulp was dewatered after impregnation.

2. Impregnating with Poly(Aluminium Sulphate)

Poly(aluminium sulphate): 20% (aluminium conc.)
Impregnating time: 30 min.

pH of the wash water was 11

TABLE II

| | Results | | |
|---|---|---|---|
| | Network strength (N) | Absorption rate (ml/s) | Total absorption (ml/g) |
| Reference | 2.9 | 1.36 | 9.52 |
| Sample | 1.7 | 5.10 | 7.88 |

EXAMPLE 3

Experimental Data

Pulp: CTMP
Pulp consistency: 3%
The pulp was taken from the dewatering press after the bleaching stage.

1. Impregnating with Waterglass

Waterglass: Sodium metasilicate
Concentration: 2.3%, 11.5% 57.6%
Impregnating time: 30 min.
The pulp was dewatered after impregnation.

2. Impregnating with Poly(Aluminium Sulphate)

Poly(aluminium sulphate): 20% (aluminium conc.)
Impregnating time: 30 min.
Wash water pH. 9

TABLE III

| | Results | | | |
|---|---|---|---|---|
| | Absorption rate (ml/s) | Total absorp. (ml/g) | Silicon conc. (g/kg) | Ash content (%) |
| Reference | 1.56 | 9.55 | 0.3 | 0.55 |
| 2.3% | 3.63 | 6.22 | 1.3 | 30.7 |
| 11.5% | 4.46 | 6.57 | — | — |
| 57.6% | 4.10 | 6.16 | — | — |

EXAMPLE 4

Experimental Data

Pulp: CTMP
Pulp concentration: 2%
The pulp was taken from the dewatering press after the bleaching stage 1. Impregnating with Waterglass Waterglass: 2.3% sodium metasilicate
Impregnating time: 30 min.
The pulp was dewatered after impregnation.

2. Waterglass Precipitation

Precipitation Method 1) pH 9
2) alum
3) poly(aluminium chloride) (PAX 11 S - Al=5.9%)
The aluminium concentration was 10% in precipitation methods 2 and 3.

Impregnating time: 30 min.

TABLE IV

| | Results | | | | |
|---|---|---|---|---|---|
| | Network strength (N) | Absorption rate (ml/s) | Total absorp. (ml/g) | Silicon (g/kg) | Ash content (%) |
| Reference | 4.8 | 1.73 | 8.94 | 0.30 | 1.59 |
| pH 9 | 4.4 | 1.76 | 9.17 | 0.30 | 1.15 |
| PAC | 5.7 | 4.00 | 9.04 | 0.85 | 2.31 |
| Alum | 4.9 | 1.88 | 9.10 | 0.65 | 1.50 |

It will be seen from Example 3 that an increase in the amount of waterglass charged to the suspension did not improve the absorption rate to any appreciable extent (see Table III).

Example 4 illustrates tests in which other chemicals than poly(aluminium sulphate) were used, namely with poly(aluminium chloride), alum and in which solely the pH-values were lowered. It will be seen from Table IV that only poly(aluminium chloride) is equally as effective as poly(aluminium sulphate). Furthermore, a further advantage afforded by poly(aluminium chloride) is that the chloride does not reduce the total absorption, as distinct from the use of the sulphate.

EXAMPLE 5

CTMP-pulp Fibres Impregnated with Poly(aluminium chloride)

Experimental Data

Pulp: CTMP
Pulp consistency: 2%
The pulp was taken from the dewatering press after the bleaching stage.

1. Impregnating with Waterglass

Waterglass: 2.3% sodium metasilicate
Impregnating time: 30 min.
General: Temperature during the impregnating process 20° C. and above 80°.

2. Impregnating with Poly(Aluminium Chloride)

Poly(aluminium chloride) (PAX 11 S - Al=5.9%). Aluminium concentration 2% and 15% respectively.
Impregnating time: 30 min.
The pH was adjusted to 9 during the impregnating process.
The pulps were washed with water and adjusted to pH 4 or to pH 11.

Results

See Tables V a and V b.

As will be seen from the following Tables, very high absorption rates were achieved in this example, the values of 5 ml/s having been obtained with an aluminium concentration of 2%. It would also seem that the wet bulk is retained to a somewhat better extent than with conventional CTMP when the pulps are loaded in a wet state, particularly at higher loads. (See Table V b). Furthermore, it would seem than a higher temperature during the impregnating process favours the absorption rate.

TABLE V a

| Pulp sample | PAC (Al. conc.) (%) | Wash Water pH | Temperature °C. | Absorp. rate (bulk - 10 cm³/g) | Total absorp. (ml/g) | Network strength (N) | Brightness (% ISO) | WRV (g/100 g) | Ash cont. (%) | Silicon cont. (g/kg) |
|---|---|---|---|---|---|---|---|---|---|---|
| Sample | 15 | 4 | 20 | 3,31 | 9,43 | 4,8 | 70,0 | 94 | 3,2 | 0,35 |
| Ref. | 0 | 11 | 20 | 2,08 | 9,23 | 6,1 | 70,4 | 112 | 1,64 | 0,3 |
| Sample | 2 | 11 | 20 | 4,50 | 9,26 | 5,5 | 69,7 | 98 | 2,1 | 2,1 |
| Ref. | 0 | 4 | 80 | 2,41 | 9,15 | 4,7 | 68,0 | 113 | 0,38 | 0,1 |
| Sample | 2 | 4 | 80 | 2,98 | 9,54 | 4,5 | 66,3 | 103 | 2,3 | 0,35 |
| Ref. | 0 | 11 | 80 | 2,63 | 9,36 | 4,9 | 68,5 | 121 | 1,42 | 0,1 |
| Sample | 2 | 11 | 80 | 5,00 | 9,16 | 5,6 | 63,0 | 114 | 3,2 | 0,9 |
| Ref. | 0 | 4 | 20 | 2,40 | 9,07 | 4,3 | 69,6 | 105 | 0,9 | 0,35 |
| Sample | 2 | 4 | 20 | 2,84 | 9,38 | 4,6 | 65,3 | 100 | 2,75 | 0,4 |

TABLE V b

| | Wet thickness Thickness (mm) at mutually different loads (kPa) | | | |
|---|---|---|---|---|
| | 0.57 | 2.5 | 5 | 7.5 |
| Ref. | 10.96 | 5.80 | 4.95 | 4.40 |
| Sample | 10.59 | 5.80 | 4.90 | 4.40 |
| Ref. | 9.36 | 5.70 | 4.70 | 4.10 |
| Sample | 8.10 | 6.10 | 4.95 | 4.20 |
| Ref. | 11.20 | 6.10 | 5.10 | 4.50 |
| Sample | 9.20 | 6.30 | 5.30 | 4.60 |
| Ref. | 8.70 | 5.90 | 4.80 | 4.20 |
| Sample | 8.30 | 6.30 | 5.20 | 4.50 |

EXAMPLE 6

Experimental Data

Pulp: CTMP
Pulp consistency: 2%
The pulp was taken immediately downstream of the bleaching tower.

1. Impregnating with Poly(Aluminium Chloride)

Poly(aluminium chloride) (PAX 11 S - Al=6.8%). The aluminium concentration was 2%.
Impregnating time: 30 min
The pH was adjusted to pH=9 during the impregnating process.
The pulps were washed with distilled water.

TABLE VI

| | Results | | | | |
|---|---|---|---|---|---|
| | Network strength (N) | Absorp. rate (ml/s) | Total absorp. (ml/g) | WRV (g/100 g) | Brightness (% ISO) |
| Reference | 5.2 | 1.28 | 9.51 | 116 | 69.8 |
| Sample | 5.8 | 3.23 | 9.66 | 109 | 70.2 |

In Example 6, the pulp was impregnated solely with poly(aluminium chloride) immediately after the bleaching tower, without previous impregnation with waterglass. A marked improvement of the absorption rate was also obtained in this case, i.e. an absorption rate of 3.23 ml/s in comparison with an absorption rate of 1.28 ml/s obtained with the reference sample.

EXAMPLE 7

Optimation of the Poly(Aluminium Chloride) Addition

Experimental Data

Pulp: CTMP
Pulp consistency: 2%
The pulp was taken from the dewatering press after the bleaching stage.

1. Impregnating with Waterglass

Waterglass: 2.3% sodium metasilicate
Impregnating time: 30 min.
General: 80° C. during the impregnating process
The pulp was dewatered subsequent to the impregnating process.

2. Impregnating with Poly(Aluminium Chloride)

Poly(aluminium chloride) PAX 11 S - Al=6.8%)
Aluminium conc. (%): 0.0, 0.05, 0.1, 0.4, 1.0, 2.0
Impregnating time: 30 min.
The pH was adjusted to pH=9 during the impregnating process.
The pulps were washed with tap water.

TABLE VII

| | Results | | | | |
|---|---|---|---|---|---|
| | Absorp.-rate (ml/s) | Total absorp. (ml/g) | Aluminium (g/kg) | Silicon (g/kg) | Ash cont. % |
| Reference | 2.77 | 9.58 | <0.1 | 0.8 | 0.85 |
| 0.05% Al | 2.99 | 9.50 | 0.3 | 0.2 | 1.17 |
| 0.1% Al | 3.08 | 9.43 | 0.6 | 0.2 | 1.14 |
| 0.4% Al | 3.43 | 9.73 | 2.5 | 0.7 | 1.57 |
| 1.0% Al | 4.28 | 9.44 | 6.6 | 1.1 | 2.73 |
| 2.0% Al | 5.22 | 9.03 | 10.3 | 1.3 | 4.25 |

When impregnating with poly(aluminium chloride), the aluminium content would appear to be fully decisive in obtaining a high absorption rate. Absorption rates of 5.22 ml/s were obtained with a 2% aluminium concentration in the impregnating solution. Additions down to 0.4% aluminium resulted in absorption rates of 3.43 ml/s. The capacity of all pulp is unchanged, with the exception of the pulps treated with the highest PAC-concentration. In this case, the network has a slightly reduced capacity, from 9.58 ml/g to 9.03 ml/g (Bee Table VII).

EXAMPLE 8

Optimizing the Silicate Addition

Experimental Data

Pulp: CTMP
Pulp consistency: 2%
The pulp was taken from the dewatering press after the bleaching stage.

1. Impregnating with Waterglass

Waterglas: Sodium metasilicate
Concentration: 0, 0.5, 1.0, 1.5, 2.0
Impregnating time: 30 min.
General: 80° C. during the impregnating process
The pulp was dewatered after impregnation.

2. Impregnating with Poly(Aluminium Chloride)

Poly(aluminium chloride) (PAX 11 S - Al=6.8%), concentration 2% aluminium.
Impregnating time: 30 min
The pH was adjusted to pH=9 during the impregnating process
The pulps were washed with water and pH-adjusted to 11.

TABLE VIII

| | | | | | | |
|---|---|---|---|---|---|---|
| | Water glass (%) | PAC | Absorp. rate (ml/s) | Total absorp. (ml/g) | Alum. (g/kg) | Silicon (g/kg) | Ash cont. (%) |
| Reference | 0 | – | 2.47 | 9.60 | <0.1 | 0.1 | 1.37 |
| Sample | 0 | + | 3.20 | 9.91 | 4.6 | 0.3 | 2.99 |
| " | 0.5 | + | 3.66 | 9.70 | 3.7 | 0.2 | 2.75 |
| " | 1.0 | + | 3.31 | 9.76 | 3.8 | 0.3 | 2.57 |
| " | 1.5 | + | 3.19 | 9.81 | 4.1 | 0.4 | 2.64 |
| " | 2.0 | + | 3.83 | 9.72 | 3.6 | 0.5 | 2.53 |

The part played by the silicate is thus not as clear as the part played by the aluminium. Furthermore, a certain amount of silicate always remains in CTMP which derives from the bleaching stage. An absorption rate of 3.20 ml/s is obtained when solely poly(aluminium chloride) is used in the total absence of waterglass.

EXAMPLE 9

The Effect of Different pH-values When Impregnating and Washing the Pulps

Experimental Data

Pulp: CTMP
Pulp consistency: 2%
The pulp was taken from the dewatering press after the bleaching stage.

1. Impregnating with Waterglass

Waterglass: 2.3% sodium metasilicate
Impregnating time: 30 min.
General: 80° C. during the impregnating process
The pulp was dewatered after impregnation.

2. Impregnating with Poly(Aluminium Chloride)

Poly(aluminium chloride) (PAX 11 S - Al=6.8%)
Concentration: 2% aluminium
The pH was adjusted to pH=9 during the impregnating process, or the prevailing pH was left unadjusted. The unadjusted impregnating solution had a pH of 4.1.
The pulps were washed with water adjusted to pH=11.

TABLE IX

| | pH at precip. | Absorp. rate (ml/s) | Total absorp. (ml/g) | Alum. (g/kg) | Silicon (g/kg) | Ash cont. (%) |
|---|---|---|---|---|---|---|
| Reference | – | 2.41 | 9.36 | – | 0.1 | 1.42 |
| Unadjusted | 4.1 | 3.42 | 9.62 | 2.02 | 0.3 | 2.44 |
| Adjusted | 9.0 | 4.61 | 9.48 | 6.07 | 0.5 | 3.12 |

EXAMPLE 10

Experimental Data

Pulp: CTMP
Pulp consistency: 2%
The pulp was taken from the dewatering press after the bleaching stage.
The impregnation processes were carried out in the following manner:

1. Impregnating with Waterglass

Waterglass: 2% sodium metasilicate
Impregnating time: 30 min.
The pulp was dewatered after impregnation.

2. Impregnating with Poly(Aluminium Chloride)

Concentration: 2% aluminium
Impregnating time: 30 min
The pH was adjusted to pH=9 during the impregnating process.
The pulps were washed with water at different pH-values of 3, 5, 7, 9 and 11 respectively.

TABLE X

| Washing at pH | Absorp. rate (ml/s) | Total absorp. (ml/g) | Ash cont. (%) | Silicon (g/kg) | Alum. (g/kg) |
|---|---|---|---|---|---|
| 3 | 2.36 | 9.39 | 1.93 | 0.4 | 8.57 |
| 5 | 2.87 | 9.59 | 2.97 | 0.6 | 13.9 |
| 7 | 4.19 | 9.24 | 3.82 | 0.7 | 14.7 |
| 9 | 4.72 | 8.89 | 4.26 | 0.8 | 15.6 |
| 11 | 3.77 | 9.42 | 3.03 | 0.6 | 5.1 |

The effect of different pH-values during and after the impregnating reaction have been investigated in Examples 9 and 10. If the pH is not adjusted during the precipitation reaction, a pH of 3–4 is obtained in the pulp suspension subsequent to adding poly(aluminium chloride). This pulp obtains a lower absorption rate than a pulp with which the pH is adjusted to pH=9 during the impregnating process (see Table IX). The pH is also highly significant when washing the pulp subsequent to the precipitation reaction (see Table X).

An optimum was obtained at pH=9, where an absorption rate of 4.72 ml/s was measured. The precipitated aluminium-silicate compounds were probably more porous at basic pH-values and became more compact at lower pH-values. Alternatively, it is conceivable that the precipitates consist of smaller particles at basic pH-values, whereas they consist of larger particles at acid pH-values. A given correlation with the aluminium content can be observed. The ash content also relates to the absorption rate, probably because the aluminium content increases.

EXAMPLE 11

The pulp used consisted of CTMP.

a) Impregnating with Waterglass and Poly(Aluminium Chloride)

A 2% sodium metasilicate concentration was used during the tests, whereafter mixing was effected by hand, by kneading for 3 minutes. The pulp consistency was adjusted from 48% to 12% during the mixing process. The pulp was then stored at 70°–75° C. for 1 hour and 24 hours respectively.

Precipitation with poly(aluminium chloride) (PAX 11 S - aluminium 7.8%, Kemira) was then effected. The concentration was 1% aluminium and mixing was effected by hand over a period of 1 or 5 minutes. During the precipitation of poly(aluminium chloride), the pulp consistency was adjusted to 7–8%. Subsequent to the mixing process, the pH-values of half of the samples were adjusted to pH 9–9.5. Those pulps whose pH-values were not adjusted had a pH of about 4. The pulps were then dried at 60° C. and defibered in Kamas.

b) Impregnating with Poly(Aluminium Chloride)

In the second experiment, solely poly(aluminium chloride) was added. Polyaluminium chloride (PAX 11S - Kemira) was added to the pulp and mixed into the pulp by hand over a period of 3 minutes. Two different concentrations of poly(aluminium chloride) were tested, 0.8% aluminium and 2.0% aluminium respectively. The pulp had a consistency of 12% during the mixing process. The pH-values of some of the pulps was adjusted to pH=9 after the mixing process. The pulp was then stored at 70°–75° C. for 1 hour and 24 hours respectively. Subsequent to this storage, the pulp was thinned to about 7% while simultaneously adjusting the pH-values of some of the pulps to pH=9. Those pulps whose pH-value was not adjusted, had a pH of about 4. The pulps were then dried at 60° C. and defibered in Kamas.

TABLE XI a

Absorption properties of the pulps subsequent to impregnating with waterglass and poly(aluminium chloride)

| Pulp sample | Mixing (min) | Storage (h) | pH-adjust. | Absorp. rate (ml/s) | Absorp. capacity (ml/g) | Network strength (N) |
|---|---|---|---|---|---|---|
| 1 | 1 | 1 | + | 4.10 | 8.38 | 2.3 |
| 2 | 1 | 1 | − | 1.10 | 9.38 | 2.7 |
| 3 | 5 | 1 | + | 3.70 | 8.70 | 2.4 |
| 4 | 5 | 1 | − | 0.91 | 9.46 | 2.5 |
| 5 | 1 | 24 | + | 4.02 | 8.78 | 2.3 |
| 6 | 1 | 24 | − | 0.06 | 9.24 | 2.5 |
| 7 | 5 | 24 | + | 4.19 | 8.70 | 2.6 |
| 8 | 5 | 24 | − | 0.09 | 9.41 | 2.4 |
| 9 * | | 1 | − | 2.22 | 9.35 | 2.3 |
| 10 * | | 24 | − | 1.88 | 9.44 | 2.8 |

* references

A factor of high significance in respect of good precipitation vis-a-vis absorption rate is the pH-adjustment, see Table XI. The absorption rate of those pulps whose pH-values were not adjusted is even lower than the absorption rates of the reference pulps. It should be noted that a high absorption capacity is obtained at low pH-values.

TABLE XI b

The absorption properties of the pulps subsequent to impregnating solely with poly(aluminium chloride)

| Pulp sample | Alum. (%) | pH-adjust. after PAC.addt. | Storage (h) | pH-adjust. after storage | Absorp. rate (ml/s) | Absorp. capac. (ml/g) | Network strength (N) |
|---|---|---|---|---|---|---|---|
| 1 | 2 | + | 1 | − | 3.76 | 8.53 | 2.5 |
| 2 | 2 | + | 24 | − | 3.39 | 8.61 | 2.4 |
| 3 | 2 | − | 1 | + | 3.64 | 8.66 | 2.8 |
| 4 | 2 | − | 1 | − | 0.62 | 8.89 | 2.5 |
| 5 | 2 | − | 24 | + | 2.88 | 9.25 | 2.2 |
| 6 | 2 | − | 24 | − | 1.50 | 9.22 | 2.4 |
| 7 | 0.8 | + | 1 | − | 2.99 | 8.90 | 2.8 |
| 8 | 0.8 | + | 24 | − | 2.90 | 9.10 | 2.5 |
| 9 | 0.8 | − | 1 | + | 1.86 | 9.13 | 2.9 |
| 10 | 0.8 | − | 1 | − | 0.44 | 9.20 | 2.8 |
| 11 | 0.8 | − | 24 | + | 2.58 | 9.36 | 3.0 |
| 12 | 0.8 | − | 24 | − | 1.28 | 9.40 | 2.3 |
| 13 | * | − | 1 | − | 2.08 | 9.18 | 2.4 |
| 14 | * | − | 24 | − | 1.82 | 9.40 | 2.7 |

* referens

TABLE XI c

The inorganic content of silicon and aluminium and the total amount in some of the pulp samples

| Pulp Sample | Silicon (g/kg) | Aluminium (g/kg) | Ash (%) |
|---|---|---|---|
| 1 | 0.8 | 14.4 | 8.68 |
| 7 | 0.8 | 6.6 | 4.85 |
| 10 | 0.8 | 5.2 | — |
| 13 | 0.6 | <0.1 | 1.40 |
| 14 | 0.6 | <0.1 | 1.34 |

These experiments also illustrate the importance of adjusting pH-values to a pH of about 9. The absorption rate of the pulps whose pH-values were not adjusted were measured as being 1 ml/s. On the other hand, the adjustment of pH-values need not necessarily take place in conjunction with charging poly(aluminium chloride) to the pulps, since pH-adjustments made after the storage period have produced an equally good effect on the absorption rate (see pulps sample 3 in Table XI b).

It is apparent from this test that a slightly higher absorption rate is obtained with a 2% aluminium concentration than with an aluminium concentration of 0.8%. The fibres precipitated with 2% aluminium also have high aluminium concentrations, and it is possible that a correlation is found with the high absorption rates, see Table XI c. Thus, the results show that good absorption rates are also achieved with precipitation tests carried out under industrially adapted conditions. In total, these tests show that it is possible to produce a fluff which has a high absorption rate solely with an addition of poly(aluminium chloride) at pH=9.

The precipitates on the pulp fibres are also manifested by markedly higher ash contents.

EXAMPLE 12

Pulp: CTMP
0.3% aluminium was added in the form of poly(aluminium chloride) and 0.5% aluminium as sodium aluminate.
Impregnating time: 1 min.
Pulp consistency: 12%
General: Impregnation was effected at 80° C.

The results of absorption assays are set forth in the following table.

TABLE XII

| | Absorption rate (ml/s) | Absorption (capacity ml/g) | Network strength (N) |
|---|---|---|---|
| Reference | 2.10 | 8.88 | 3.4 |
| Sample | 3.88 | 9.22 | 4.1 |
| Sample | 4.32 | 9.01 | 5.1 |

This example shows that absorption rate is significantly improved even with high pulp consistencies.

The fibre impregnated with aluminium salt in accordance with the present invention has also been tested with respect to its behaviour in sanitary products. Such products include an absorption body made of fluff, in order to impart to the product volume, shape stability and absorbency in combination with a certain ability to store or contain liquid. In order to improve liquid retention, so-called superabsorbents have been incorporated in such bodies, the function of these superabsorbents being to contain liquid and also to retain liquid under pressure.

One problem in this respect, however, is that high proportions of superabsorbents are liable to result in blocking effects which impede dispersion of liquid throughout the absorbent body. Present day absorbent bodies intended for the aforesaid purpose will normally include about 10–30% superabsorbents.

Improved properties can be obtained, particularly improved absorption rates and improved liquid dispersion to the peripheral parts of the product, can be achieved by replacing the superabsorbents, either completely or partially, or supplementing said superabsorbents with cellulose fibres impregnated with an aluminium salt in accordance with the invention.

The inventive aluminium-salt-impregnated fibre is present in an amount corresponding to 10–100% of the weight of the absorption material.

EXAMPLE 13

The impregnated fibre used was produced in the following manner:

Experimental Data

Pulp: CTMP
Pulp consistency: 2%
The pulp was taken from a dewatering press after the bleaching stage 1. Impregnating with Waterglass Waterglass: 2.3% sodium metasilicate
Impregnating time: 30 min.
General: The impregnating process was carried out at 80° C. The pulp was dewatered after the impregnating process.

2. impregnating with Poly(Aluminium Chloride)

Polyaluminium chloride (PAX 11S - Al=6.8%)
Concentration: 2% aluminium
The pH was adjusted to pH=9 during the impregnating process.
The pulps were washed with water adjusted to pH 11.
The pulps were defibered in Kamas, which resulted in a knot content number of at most 10%.

The material used to carry out the dispersion measurements had a grammage of about 500 g/m² and a bulk density of 12 cm³/g. In addition to forming a network of reference pulp and of the fibre pulp impregnated with aluminium-salt, a mixture of these pulps was also formed (50%/50%).

a) Absorption Properties

The absorption properties were measured with the aid of "Porous Plate Testing Apparatus" and the following results were obtained:

TABLE XII a

| | Absorption rate (ml/s) | Total absorption (ml/g) |
|---|---|---|
| Reference | 2.16 | 8.32 |
| Sample | 4.35 | 8.29 |
| Reference/sample (50%/50%) | 3.66 | 8.69 | b) Measuring the Capillary Rise

The fibres impregnated with aluminium salt have also been evaluated together with a superabsorbent "Salsorb 84" (Allied Colloids Ltd) in a 10% admixture. The superabsorbent was sieved-in between two formed pulp networks. The network had a size of 30×130 (mm) and the surface weight or grammage was about 500 g/m². This sample body was then compressed between two plexi-glass plates, to a bulk density of 7 cm³/g.

The whole of the sample package was then lowered into a vessel containing 0.9% NaCl. The liquid level in the sample was read off at five second intervals over a period of 60 seconds, and then in intervals of 10 seconds over a period of 120 seconds. The results are set forth in Table XIII b, from which it will be seen that in fibre networks containing superabsorbents the fibres impregnated with aluminium salt absorbed liquid more rapidly than conventional CTMP-pulp and that the liquid was absorbed to a greater height in the inventive material than the conventional pulp.

TABLE XII b

| Time (s) | Reference absorb. height (mm) | | Sample absorb. height (mm) | |
|---|---|---|---|---|
| | 1 | 2 | 1 | 2 |
| 5 | 23 | 25 | 30 | 32 |
| 10 | 30 | 32 | 40 | 41 |
| 15 | 37 | 40 | 48 | 50 |
| 20 | 44 | 44 | 53 | 55 |
| 25 | 50 | 50 | 57 | 60 |
| 30 | 54 | 55 | 61 | 63 |
| 35 | 59 | 59 | 63 | 66 |
| 40 | 62 | 62 | 70 | 70 |
| 45 | 64 | 65 | 72 | 73 |
| 50 | 66 | 67 | 75 | 75 |
| 55 | 69 | 69 | 77 | 79 |
| 60 | 70 | 70 | 80 | 82 |
| 70 | 73 | 73 | 83 | — |
| 80 | 77 | 76 | 86 | 86 |
| 90 | 80 | 79 | 90 | 89 |
| 100 | 83 | 82 | 92 | 95 |
| 110 | 85 | 86 | 100 | 99 |
| 120 | 89 | 90 | 102 | 101 | c) Measuring Dispersion on PFI-Sample Bodies X, Y and Z Directions

In one experiment "Salsorb 84" (superabsorbent) was admixed with pulp and sample bodies were formed on PFI. In this case, 20% superabsorbents were admixed homogenously with the pulp. The sample bodies were evaluated in an X, Y and Z-direction absorption/dispersion meter. The apparatus used was a dispersion meter produced by Holger Hollmark at STF1, Stockholm. (SCAN P 39 X, Holger Hollmark and Per-Olof Bethge, "Water absorption rate and capacity").

The fibre material used for this test was defibered in a Kamas-mill. An 8 mm screen was used in the defibering process and the input speed was 2 g/s. The results are set forth in the following table, XIII c.

TABLE XIII c

| | X-direction | Y-direction | Z-direction |
|---|---|---|---|
| Reference | 7.17 | 8.41 | 5.37 |
| Sample | 5.85 | 5.99 | 3.46 |

The liquid is seen to disperse in the three directions of the network of aluminium-silicate fibres more rapidly than in conventional CTMP, even at this high proportion of superabsorbent in admixture with the fibres.

The dispersion of liquid in the horizontal direction is markedly improved in the case of the aluminium-silicate network.

The aluminium-silicate fibres together with superabsorbents also have improved liquid-dispersion ability in both the horizontal and vertical directions.

EXAMPLE 14

Rewetting

Because sanitary articles in the form of diapers and incontinence guards are often wetted several times in use, the inventive fibres have also been tested by wetting the fibres twice in succession. The amount of superabsorbent ("Salsorb 84") admixed with the fibres was 10%.

TABLE XIV

| | Absorption time (s) | |
|---|---|---|
| | Wetting I | Wetting II |
| Inventive fibres | 6.01 | 10.23 |
| Reference fibres | 27.81 | 49.39 |

In this case, the time measured was the time taken for a given quantity of liquid to be absorbed in the pulp. It was found that the fibres impregnated with aluminium salt are able to absorb liquid more quickly than the reference fibres, even when wetted a second time.

It would be possible to use these fibres as a dispersion layer in a product, due to their unique ability to disperse liquids. In many diapers, the absorption body or pad comprises two or more layers. One or more of the diaper layers located nearest the backing sheet of the diaper could appropriately comprise fibres produced in accordance with the invention, either totally or partially.

When combined with superabsorbents, the fibres have a high liquid-transport ability, a feature which can be utilized in sanitary products.

The novel pulp can also replace superabsorbents in diapers to a given extent.

EXAMPLE 15

Unbleached CTMP, i.e. pulp which does not contain silicate residues, was impregnated, at a pulp consistency of 2%, with poly(aluminium chloride) solution in an amount corresponding to 2% aluminium. The pH of the pulp suspension was adjusted to about pH=9. The following absorption properties were measured.

TABLE XV

| Aluminium conc. (%) | Absorption rate (ml/s) | Absorption capacity (ml/g) |
|---|---|---|
| 0 | 0.88 | 9.96 |
| 2 | 3.32 | 10.09 |

It will be seen from this example that when impregnating cellulosic fibres in an aqueous suspension, the absorption rate increases by a factor of 3.8, even in the case where no silicate was present.

EXAMPLE 16

In order to show the effect obtained when impregnating synthetic fibres in accordance with the invention, synthetic fibres, polyester fibres (from Du Pont, trade name Dacron D342 N5D), having a a length of 6 mm were treated with an aluminium-silicate complex. The polyester fibres were first impregnated with sodium metasilicate over a period of 10 minutes. The fibres were then impregnated with poly(aluminium chloride) and the pH adjusted to pH=9.

TABLE XVI

| Sodium silicate (%) | Aluminium conc. (%) | Absorp. rate (ml/s) | Absorp. capacity (ml/g) |
|---|---|---|---|
| 0 | 0 | 0.01 | 0.18 |
| 0 | 2 | 0.65 | 10.19 |
| 2 | 2 | 0.51 | 10.03 |

It will be seen from this table that when treating fibres solely with aluminium salt the absorption rate was increased by a factor of 65, whereas in the case of fibres treated with a combination of sodium metasilicate and poly(aluminium chloride) the absorption rate increased by a factor of 51.

EXAMPLE 17

Fibres originating from chemical pulp were impregnated with poly(aluminium chloride), by precipitation on bleached softwood sulphate. Immediately after adding the poly(aluminium chloride), the pH was adjusted to pH=9 with an NaOH addition. The pulp suspension was stirred continuously for 10 minutes.

TABLE XVII

| Aluminium conc. (%) | Absorption rate (ml/s) | Absorption capacity (ml/g) |
|---|---|---|
| 0 | 4.14 | 8.17 |
| 2.1 | 5.89 | 7.90 |

It will be seen that a marked increase in the absorption rate was obtained, again by a factor of 1.4.

EXAMPLE 18

A fibre suspension where the fibres originated from CTMP-pulp was impregnated with 2.3% sodium metasilicate for 30 min. Poly(aluminium chloride) was then added in a quantity corresponding to 15% aluminium. The pH of the pulp suspension was adjusted to pH=11.

TABLE XVIII

| | Absorption rate (ml/s) | Aluminium content of the fibre (g/kg) |
|---|---|---|
| Sample | 5.20 | 38 |
| Reference | 2.63 | 0.1 |

It will be seen from this that a satisfactory increase in the absorption rate was obtained when a large amount of aluminium was added.

EXAMPLE 19

CTMP-fibres in the form of an aqueous suspension were impregnated in part solely with sodium aluminate ($Na_2Al_2O_4$) and in part with a combination of sodium aluminate and poly(aluminium chloride), with and without treating the fibres with waterglass.

The impregnation time was 10 minutes, with the exception of samples 18–21 where the impregnation time was 3 minutes. The pulp consistency used in samples 18–21 was 6% instead of 2%, this latter consistency being the consistency used in all other samples.

When solely sodium aluminate was used, which has a high pH of about 14, the pulp suspension has a similarly high pH of about 11–12.

When necessary, the pulp suspension was adjusted with acid or base respectively.

Subsequent to impregnation, the pulp was formed into sheets on a Büchner funnel and dried at 23° C. to a relative moisture content of 50%. Defibering was carried out in a Kamas-mill having an 8 mm screen, at an infeed speed of 2 g/s. A specific reference pulp was produced for the majority of samples, where treatment was carried out in the same manner as for the sample pulp, but with tap water.

Absorption rate and total absorption was then established at a bulk density of 10 $cm^3$/g and at a load of 2.5 kPa, the aluminium content being determined by ICP-inductively coupled plasma.

Thus, these tests were carried out at mutually different aluminium concentrations when impregnating with poly-(aluminium chloride) in combination with sodium aluminate and with solely sodium aluminate respectively, and at varying pH-values. Furthermore, the tests were carried out either with or without impregnating the fibres with waterglass. The results are set forth in the following table XIX.

It will be seen from the table that the pH-value is important in achieving improved absorption properties, wherein a pH-value of about 9 provides optimum results, both when impregnating solely with sodium aluminate and when impregnating with a combination of sodium aluminate and poly(aluminium chloride). Impregnation should thus be effected at a pH above 5 and below pH 11, in order to obtain an improved absorption rate. It will also be seen that the absorption rate is totally dependent on the amount of aluminium added to the system, whereas impregnation with waterglass favours an increase in absorption rate to a lesser extent. On the other hand, it is evident that the combination of sodium aluminate and poly(aluminium chloride) results in a marked improvement of the absorption rate.

TABLE XIX

| Pulp sample | Water-glass (%) | Aluminium conc. as polyalumin. chloride (%) | Aluminium conc. as sodium aluminate (%) | pH at impreg. | Aluminium retention (%) | Absorp. rate (ml/s) | Total absorp. (ml/g) | Reference pulp absorp. rate (ml/s) Total absorp. (ml/g) |
|---|---|---|---|---|---|---|---|---|
| 1 | 2.3 | 0.5 | 0.4 | 8* | 87 | 5.0 | 8.95 | |
| 2 | 2.3 | 0.5 | 0.4 | 8* | 90 | 4,4 | 8,98 | |
| 3 | 1 | 0.2 | 0.2 | | 95 | 3.75 | 9,21 | 2,21 resp. |
| 4 | 2 | 0.2 | 0.2 | | 94 | 3.50 | 9.44 | 9,14 |
| 5 | 0 | 0.2 | 0.7 | 9.8 | — | 4.97 | 9.42 | 2,02 resp. |
| 6 | 0 | 0.7 | 0.2 | 4.6 | — | 2.25 | 9.80 | 9,38 |
| 7 | 1 | 0.2 | 0.7 | 9,3 | — | 4,21 | 9.60 | 2,10 resp. |
| 8 | 1 | 0.7 | 0.2 | 4,6 | — | 1,83 | 9.74 | 9,60 |
| 9 | 0 | 0.1 | 0.1 | 8.3 | — | 1,69 | 9,49 | 2.10 resp. |
| 10 | 0 | 0.1 | 0.3 | 9.7 | — | 2,66 | 9.57 | 9,37 |
| 11 | 0 | 0.1 | 0.5 | 9,9 | — | 2,78 | 9.55 | 9,37 |
| 12 | 0 | 0.2 | 0.3 | 9.0 | — | 3,22 | 9,72 | 2,06 resp. |
| 13 | 0 | 0.2 | 0.5 | 9.4 | — | 3,50 | 9,65 | 9,54 |
| 14 | 1 | 0.2 | 0.3 | 9.0 | — | 3,62 | 9,58 | |
| 15 | 1 | 0.2 | 0.5 | 9,4 | — | 3,80 | 9,60 | |
| 16 | 2 | 0 | 2 | ca 11,0 | — | 3.96 | 9,58 | 2.55 resp. |
| 17 | 2 | 0 | 2 | 9* | — | 5,52 | 8,68 | 9.45 |
| 18** | 0 | 0,25 | 0,7 | 10 | — | 3,90 | — | 2,48 |
| 19** | 0 | 0,3 | 0,7 | 9.9 | — | 4.08 | — | 2,48 |
| 20** | 0 | 0,4 | 0,8 | 9.9 | — | 4,48 | — | 2,48 |
| 21** | 0 | 0,5 | 0,9 | 9.9 | — | 4,49 | — | 2,48 |
| 22** | 0 | 0.2 | 0.7 | 10,2 | — | 4,00 | 8.92 | 2.20 resp. |
| 23** | 0 | 0,2 | 0,7 | 10,2 | — | 3,14 | 9.62 | 9,10 |
| 24** | 0 | 0,2 | 0,7 | 10,2 | — | 3,14 | 9.38 | 9,10 |
| 25** | 0 | 0.3 | 0,7 | 9.8 | — | 4,06 | 9.30 | 2.56 resp. 9.04 |

*pH has been adjusted with an acid or a base
** process water has been used

The following Examples 20–23 illustrate embodiments of the invention in which the fibres are first impregnated with alkali silicate and thereafter with aluminium salt.

In order to increase the porosity of the fibres, and thereby improve the take-up of alkali silicate in the fibre walls, the fibre material can be milled prior to suspending the fibres in water and subjecting said fibres to subsequent chemical treatment, such that the fibre structure is loosened or disintegrated and the specific surface area of the fibre therewith increased. Impregnation with alkali silicate is also favoured by an increase in temperature to 30°–90° C., preferably 50°–80° C., which lies close to the temperature of the process water. The fibre pulp is preferably impregnated, by spraying an alkali-silicate solution onto the pulp.

A non-dried, bleached softwood sulphate pulp and CTMP-pulp respectively were used in the following example. The absorption rate, determined by "demand wettability" was measured in order to illustrate the improvement achieved with regard to the absorption properties of fibre material that has been treated by means of the inventive method.

The amount of liquid absorbed over a given period of time was registered automatically, while at the same time registering the thickness of the sample body when subjected to a load of 2.5 kPa. The absorption rate is determined through the linear, initial liquid absorption phase. The sample bodies were produced in accordance with a method devised by J. W. Brill, "New Scandinavian Fluff Test Methods", TAPPI Journal, Vol. 66, No. 11, 1983.

EXAMPLE 20

A 10%-sodium silicate solution having a ratio of $$3.2 \left( \frac{\text{weight \% SiO}_2}{\text{weight \% Na}_2\text{O}} \right)$$

was added to a non-dried, bleached softwood sulphate pulp having a dry content of 50%, such that the mixture had a fibre content of 4%. The fibre suspension was then stirred for 60 minutes and thereafter dewatered. A 35%-poly(aluminium sulphate) solution ("PAX 7OP") having a basicity of 21.6% and an aluminium content of 8.5% was then added to the solution and the solution subsequently stirred for 30 minutes, whereafter the suspension was dewatered and the fibre pulp washed with alkaline washing water (pH=11), and then dewatered and dried. The pulp was defibered in a laboratory hammer mill and thereafter formed into circular fluff bodies. The absorption rate of the treated fibre pulp was 4.80 ml/s, whereas the absorption rate of a referenced pulp which had not been treated in accordance with the invention was measured as 3.12 ml/s.

EXAMPLE 21

The method described in Example 20 was repeated, but in this case a CTMP-pulp was impregnated instead of a softwood sulphate pulp.

The absorption rate of the treated CTMP-fibres was 4.16 ml/s, whereas the measured absorption rate of the reference pulp was 1.36 ml/s.

EXAMPLE 22

The method described in Example 21 was repeated, but instead of using poly(aluminium sulphate), the silicate was precipitated with a 10%-poly(aluminium chloride) solution (aluminium content 5.9% and OH/Al=1.6). Subsequent to being dewatered, the pulp was washed at pH=9, dewatered and dried. The measured absorption rate of the treated CTMP-fibres was 3.58 ml/s, whereas the measured absorption rate of the reference pulp was 1.72 ml/s.

EXAMPLE 23

A CTMP-pulp taken directly after the bleaching stage was precipitated with poly(aluminium chloride) (aluminium content 5.9% and OH/Al=1.6) with a concentration of 2% calculated on the quantity of pulp present. The pulp suspension was stirred for 30 minutes and then dewatered, whereafter the pulp was thoroughly washed and again dewatered and then dried. The measured absorption rate of the treated CTMP-fibres was 3.23 ml/s whereas the measured absorption rate of the reference pulp was 1.28 ml/s.

EXAMPLE 24

A CTMP-pulp is impregnated with $AlCl_3 \times 6H_2O$ for 10 minutes. The pH of the pulp suspension is adjusted to 8 at the $AlCl_3 \times 6H_2O$ addition (2% aluminium). After the impregnation, the pulp is dewatered and dried.

|  | Absorption rate (ml/s) |
| --- | --- |
| Reference | 2.48 |
| Sample | 3.98 |

EXAMPLE 25

A CTMP-pulp is impregnated with $Al_2(SO_4) \times 18H_2O$ for 10 minutes. The pH of the pulp suspension is adjusted to 7.5 at the addition of chemicals. The pulp is dewatered and dried in 40° C.

|  | Absorption rate (ml/s) |
| --- | --- |
| Reference | 2.31 |
| Sample | 3.71 |

I claim:

1. Aluminum-salt impregnated organic pulp fibers, showing improved liquid dispersion properties in horizontal and vertical direction in an absorption body which includes said fibers, for use in absorption articles, wherein the fibers have an increased absorption rate improved by the impregnation by a factor of 1.3–4, and wherein the fibers have an aluminum content of 3–100 g/kg, calculated on dry pulp, said fibers having been impregnated with aluminum salt in aqueous solution at a pH of 5–11, said fibers being dried and in the form of fluff.

2. Fibers according to claim 1, wherein the aluminum salt is selected from the group consisting of poly(aluminum chloride) and poly(aluminum sulphate).

3. Fibers according to claim 1, wherein the aluminum salt is sodium aluminate.

4. Fibers according to claim 1, wherein the pH is 8.5–9.5.

5. Fibers according to claim 1, wherein the pH is 9.

6. Fibers according to claim 1, wherein silicate is present when impregnating with aluminum salt.

7. Fibers according to claim 1, wherein the fibers originate from a member selected from the group consisting of CTMP-cellulose pulp and chemical cellulose pulp.

8. A method for producing organic pulp fibers with aluminum salt, whereby the fibers have improved liquid dispersion properties in horizontal and vertical direction in an absorption body which includes said fibers, comprising impregnating fibers in the form of an aqueous suspension with an aluminum salt solution at a pH of 5–11; adding the aluminum salt to the fiber suspension while stirring the suspension, the aluminum salt solution used for the impregnation process being an aqueous solution of such concentration that the aluminum content of the fiber pulp is 3–100 g/kg, calculated on dry pulp; and drying said fibers, said dried fibers being in the form of fluff.

9. A method according to claim 8, wherein the aluminum salt is selected from the group consisting of poly(aluminum chloride), poly(aluminum sulphate), poly(aluminum phosphate), sodium aluminate and mixtures thereof.

10. A method according to claim 8, wherein silicate is added in the form of residual silicate derived from a hydrogen peroxide stage of a bleaching process.

11. A method according to claim 8, wherein the fibers originate from a member selected from the group consisting of CTMP-cellulose pulp and chemical cellulose pulp.

12. A method according to claim 8, wherein the fibers, in the form of a suspension having a solids content of at least 2%, are impregnated in a first stage with an alkali silicate solution in an amount of 0.05–20% by weight, calculated on the dry weight of the fiber pulp, at a pH-value of 10.0–13 while vigorously stirring the suspension, whereafter the fiber suspension is dewatered and treated in a second stage with an aluminum salt solution at a pH-value of 5–11, followed by washing and drying of the pulp fibers.

13. A method according to claim 12, wherein subsequent to being treated with an aluminum salt solution, the fiber suspension is thinned with water and made alkaline to a pH-value above 8.0.

14. A method according to claim 8, wherein impregnation is effected under vacuum conditions.

15. A method according to claim 8, wherein subsequent to impregnation with the alkali silicate solution, the fiber suspension is passed to a retention vessel to achieve complete diffusion of the alkali silicate solution into the fiber walls, prior to dewatering the fiber suspension.

16. A method according to claim 8, wherein the fiber material is subjected to a beating process prior to being suspended in water and impregnated, so as to increase the porosity of the fibers.

17. A method according to claim 8, wherein the fibers are impregnated at a temperature of 30°–90° C.

18. Fibers produced by the method of claim 8.

19. An absorption material for use in sanitary articles, wherein the material consists essentially of dried fibers that have been impregnated with aluminum salt and are in the form of fluff and have an aluminum content of 3–100 g/kg.

20. An absorption material according to claim 19, wherein the quantity of aluminum-salt-impregnated fibers in said material is 10–100%, calculated on the weight of the absorption material.

21. Fibers according to claim 1, wherein said pH is 7–11.

22. A method according to claim 8, wherein said pH is 7–11.

* * * * *